(12) United States Patent
Wayd et al.

(10) Patent No.: US 9,107,735 B2
(45) Date of Patent: Aug. 18, 2015

(54) HINGE FOR KNEE JOINT ORTHOSES, KNEE JOINT PROSTHESES AND/OR BRACES

(75) Inventors: Kurt Wayd, Vienna (AT); Josef Grafinger, Vienna (AT); Albert Frass, Mödling (AT)

(73) Assignee: Kurt Wayd, Wien (AT)

( * ) Notice: Subject to any disclaimer, the term of this patent is extended or adjusted under 35 U.S.C. 154(b) by 290 days.

(21) Appl. No.: 13/473,214

(22) Filed: May 16, 2012

(65) Prior Publication Data

US 2013/0018293 A1     Jan. 17, 2013

(30) Foreign Application Priority Data

May 19, 2011 (AT) .................................. A 718/2011

(51) Int. Cl.
    *A61F 5/01*      (2006.01)
(52) U.S. Cl.
    CPC ....... *A61F 5/0123* (2013.01); *A61F 2005/0146* (2013.01)
(58) Field of Classification Search
    CPC ....... A61F 5/01; A61F 5/0102; A61F 5/0123; A61F 5/0125; A61F 2005/0146; A61F 2005/0148
    USPC ......... 602/5, 16, 20, 23, 26–29; 128/878, 882
    See application file for complete search history.

(56) References Cited

U.S. PATENT DOCUMENTS

| | | | | |
|---|---|---|---|---|
| 911,243 | A * | 2/1909 | Johannesen | 602/16 |
| 3,826,251 | A * | 7/1974 | Ross | 602/16 |
| 4,320,747 | A * | 3/1982 | Daniell, Jr. | 602/16 |
| 4,723,539 | A * | 2/1988 | Townsend | 602/16 |
| 4,773,404 | A * | 9/1988 | Townsend | 602/16 |
| 4,890,607 | A * | 1/1990 | Townsend | 602/26 |
| 5,031,606 | A * | 7/1991 | Ring, Sr. | 602/16 |
| 5,168,865 | A * | 12/1992 | Radcliffe et al. | 602/16 |
| 5,230,696 | A * | 7/1993 | Silver et al. | 602/16 |
| 5,244,455 | A * | 9/1993 | Swicegood et al. | 602/16 |
| 5,330,418 | A * | 7/1994 | Townsend et al. | 602/26 |
| 6,436,018 | B2 * | 8/2002 | Pellis | 482/136 |
| 6,488,711 | B1 * | 12/2002 | Grafinger | 623/20.24 |
| 7,083,583 | B2 * | 8/2006 | Opahle et al. | 602/16 |
| 7,435,234 | B2 * | 10/2008 | Gamada | 602/26 |
| 7,597,716 | B2 * | 10/2009 | Grafinger | 623/39 |
| 7,849,828 | B2 * | 12/2010 | Elnick et al. | 123/90.39 |
| 2012/0253235 | A1 * | 10/2012 | Pellis | 600/595 |

* cited by examiner

*Primary Examiner* — Alireza Nia
*Assistant Examiner* — Raymond E Harris
(74) *Attorney, Agent, or Firm* — Dykema Gossett PLLC

(57) ABSTRACT

A hinge for knee joint orthoses, prostheses and/or braces includes first and second hinge brackets overlappingly connected to each other at their ends so that with increasing angle therebetween, a combined rolling and sliding movement is effected in a plane defined by the two hinge brackets. Curves and guide elements at the overlapping ends of the hinge brackets interact such that with increasing angle therebetween, a combined rolling and sliding movement of the second hinge bracket is effected in the plane defined by the two hinge brackets in a direction which leads substantially radial to the axis of the first hinge bracket into the quadrant enclosed between the two hinge brackets, wherein the center of rotation of the two hinge brackets remains substantially stationary for an angle between the hinge brackets of between 0 and 25°.

5 Claims, 4 Drawing Sheets

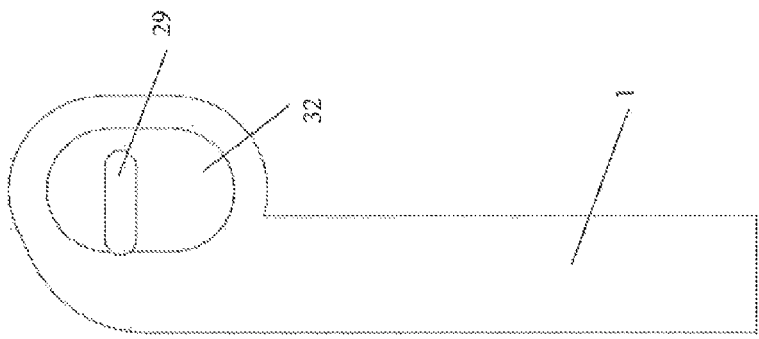
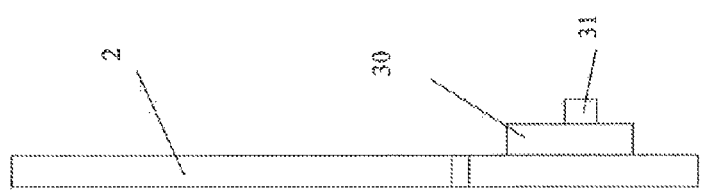
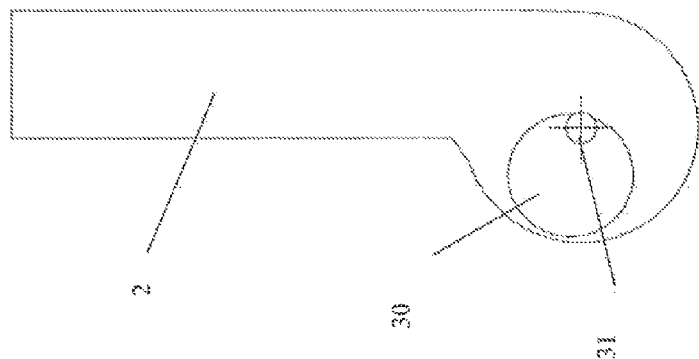

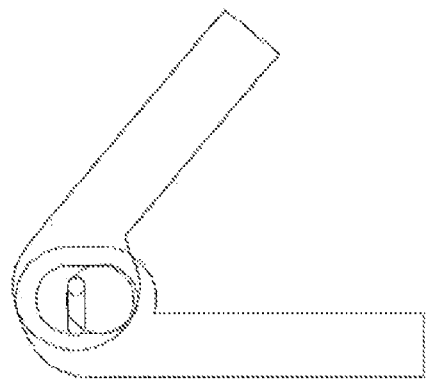
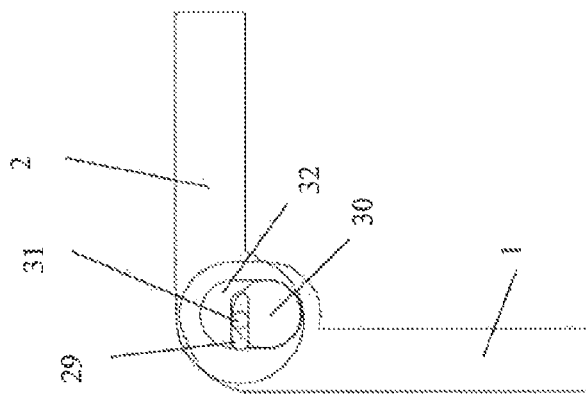
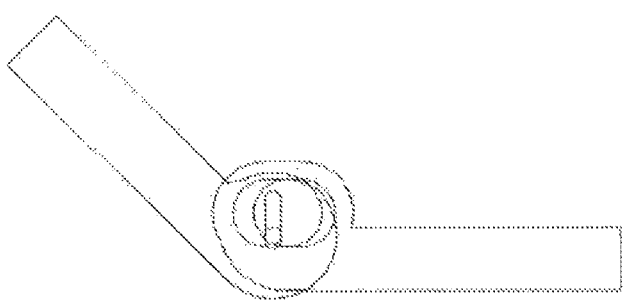
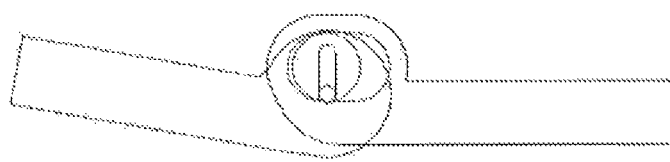
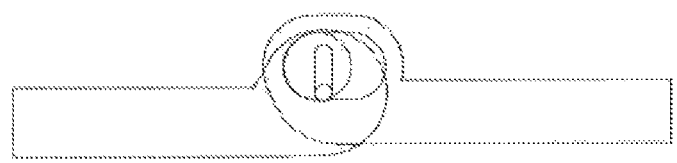

HINGE FOR KNEE JOINT ORTHOSES, KNEE JOINT PROSTHESES AND/OR BRACES

BACKGROUND OF THE INVENTION

The invention relates to a hinge for knee joint orthoses, knee joint prostheses and/or braces that includes at least one first hinge bracket assigned to the lower leg and at least one second hinge bracket assigned to the upper leg, which hinge brackets are overlappingly connected to each other with their ends in such a manner that with increasing angle between the hinge brackets, a combined rolling and sliding movement is effected in the plane defined by the two hinge brackets, wherein in the overlapping end of one hinge bracket, curves are cut out and at the overlapping end of the other hinge bracket, guide elements interacting with the curves of the other hinge bracket are provided.

The terms "rotating", "rolling" and "sliding" are interpreted differently in connection with the movements taking place in a knee joint. A rotational movement in the technical meaning is usually the rotation of a body about a stationary axis. A rolling movement in the technical meaning can be compared with a wheel that rolls on a flat surface, wherein the center of the wheel moves in the direction of the rolling movement. A sliding movement in the technical meaning is the displacement of a body relative to another body or to its underlying surface, comparable to a blocked wheel that is displaced on a flat surface (e.g., skid mark).

A simultaneous rolling and sliding movement as it takes place in the knee joint is comparable in this context with a wheel that rolls on a flat surface wherein, however, the center of rotation is displaced in the direction of the movement by a value that is smaller or greater as it would mathematically correspond to the rolling movement (analogous to spinning or locking wheels of a vehicle).

The object of the present invention was a hinge of the aforementioned type which, by means of a variable center of rotation, optimally recreates the kinematics of the natural human knee.

SUMMARY OF THE INVENTION

In order to achieve this object, the invention is characterized in that the curves are configured such that with increasing angle between the hinge brackets, a combined rolling and sliding movement of the second hinge bracket is effected in the plane defined by the two hinge brackets in a direction which leads substantially radial to the axis of the first hinge bracket into the quadrant enclosed between the two hinge brackets, wherein the center of rotation of the two hinge brackets remains substantially stationary for an angle between the hinge brackets of between 0 and 25°.

According to a first embodiment of the invention, a first opening is cut out in the first hinge bracket as a substantially straight slot and a second opening is cut out curved around the slot as the center, wherein with increasing angle, the displacement of the guide element in the second opening effects a preferably progressive displacement of the other guide element in the slot.

Advantageously, in one of the hinge brackets two openings are cut out in a slotted shape, wherein with increasing angle between the hinge brackets, the relative course of the openings effects a displacement of the second hinge bracket substantially radial to the axis of the first hinge bracket into the circle segment enclosed between the two hinge brackets, wherein the two curves are preferably bent and face each other with their concave sides.

In contrast to this, in another embodiment of the invention one of the hinge brackets has an opening into which the other hinge bracket protrudes, wherein the inner surface of the hollow body forming the opening has at least two curved segments against which at least two cam-shaped outer contours of the other hinge bracket rest as guide elements.

In a still further embodiment of the invention a first and essentially straight recess is provided in the first hinge bracket, which recess runs essentially parallel to the longitudinal axis of the hinge bracket, a further essentially straight slot with smaller width than the recess is provided in the first hinge bracket and oriented essentially perpendicular to the recess, whereby the second hinge bracket carries two essentially circular guide elements, the first guide element proximately adjacent the hinge bracket being positioned eccentrically and having a diameter corresponding essentially to the width of the recess on the first hinge bracket, and the second guide element being provided on the first guide element, having a diameter corresponding essentially to the width of the straight slot and being positioned essentially in the center of the end part of the second hinge bracket, which end part is overlapping with the first hinge bracket. This allows a relatively simple and cheap production as well as an orthopedically optimal reproduction of the relative movement of the hinge brackets during the bending and/or stretching movement.

In order to additionally enable an adaptation to the respective varus or valgus position of the knee and also an absorption of lateral movements as well as optionally a correction of pathological malpositioning, an embodiment is provided in which at least one of the overlapping regions of at least one of the hinge brackets is connected to the hinge bracket's section adjacent thereto via a monocentric hinge, the axis of which is oriented substantially parallel to the plane defined by the angular movement of the two hinge brackets.

If according to another optional feature of the invention, at least one of the overlapping regions of at least one of the hinge brackets is connected to the hinge bracket's section adjacent thereto via two hinge elements which enable rotational movement between the support body and the orthosis hinge and/or knee joint brace hinge about the axis of the lower leg, the rotation of the lower leg about its longitudinal axis, which is physiologically possible when the knee is bent, can take place.

Another optional feature provides that at least one of the overlapping regions of at least one of the hinge brackets is connected to the hinge bracket's section adjacent thereto via a length adjustment system which enables a change of the gap between the section overlapping the other hinge bracket and the remaining portion of the hinge bracket. The advantage of the length adjustment is the reduction of the load which is exerted by the femoral condyles to the tibial plateau.

Also suited for achieving the given object is a knee orthosis having at least two first hinge brackets assigned to the lower leg and at least two second hinge brackets assigned to the upper leg, which hinge brackets are connected in each case via a hinge according to any one of the preceding paragraphs, wherein the two hinges or their centers of rotation are located at different heights in order to allow an adaptation to the respective varus or valgus position of the knee, for example.

BRIEF DESCRIPTION OF THE DRAWINGS

In the following description, the invention shall be explained in more detail by means of preferred but not limiting exemplary embodiments and with reference to the attached drawings.

FIGS. 5a to 5h show a further embodiment of a hinge according to the invention in plain and side view as well as in different positions during bending.

DETAILED DESCRIPTION OF THE PREFERRED EMBODIMENTS

Figure 1:
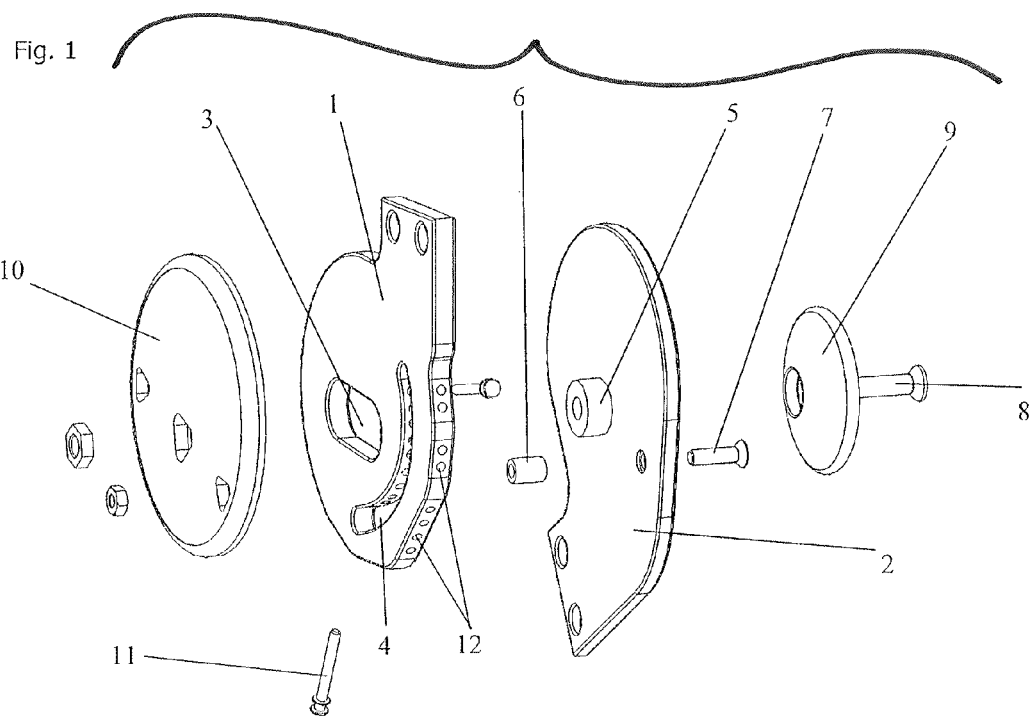
FIGS. 1 to 4 each show different embodiments of a hinge according to the invention in an exploded view.

The main function of the hinge according to the present invention is the recreation of the kinematics of the human knee in order to obtain, when using the hinge in knee joint prostheses, orthoses or braces, a rotational center that is variable in such a manner that no stresses can be generated in the prosthesis or orthosis which are perceived by the wearer or patient as being unpleasant or impairs the mobility of the leg.

For this purpose, the hinge comprises at least one first generally flat hinge bracket 1 assigned to the lower leg and at least one generally flat second hinge bracket 2 assigned to the upper leg, which hinge brackets are overlappingly connected with their ends. In the embodiment illustrated in FIG. 1, two openings 3, 4 are cut out in the first hinge bracket 1. A first opening 3 is formed as a substantially straight slot, while the second opening 4 is curved and cut out around the slot 3 as the center. At the second hinge bracket 2, two guide elements 5, 6 are provided wherein in each case one guide element 5 and 6 engages in one of the openings 3 and 4, respectively, and is displaceable therein along the openings 3, 4. During the bending movement of the two hinge brackets 1, 2 relative to each other, the guide element 6 engaging in the second opening 4 is guided corresponding to the curvature of the opening 4, which movement of the guide element 6 along the curved path keeps the center of rotation of the two hinge brackets 1, 2 substantially stationary up to an angle between the hinge brackets 1, 2 of 25°.

When continuing the bending movement of the hinge brackets 1, 2, the further preferably progressive movement of the guide element 6 then also effects in the opening 4 a continuing displacement of the other guide element 5 in the straight opening 3. The movement which in the case of a stationary center of rotation is a purely rotational movement then transitions with increasing angle between the hinge brackets 1, 2 into a combined rolling and sliding movement in a plane defined by the two hinge brackets 1, 2, which plane guides the center of rotation in a preferably progressive manner radial to the axis of the first hinge bracket 1 into the quadrant enclosed between the two hinge brackets 1, 2.

Figure 2:
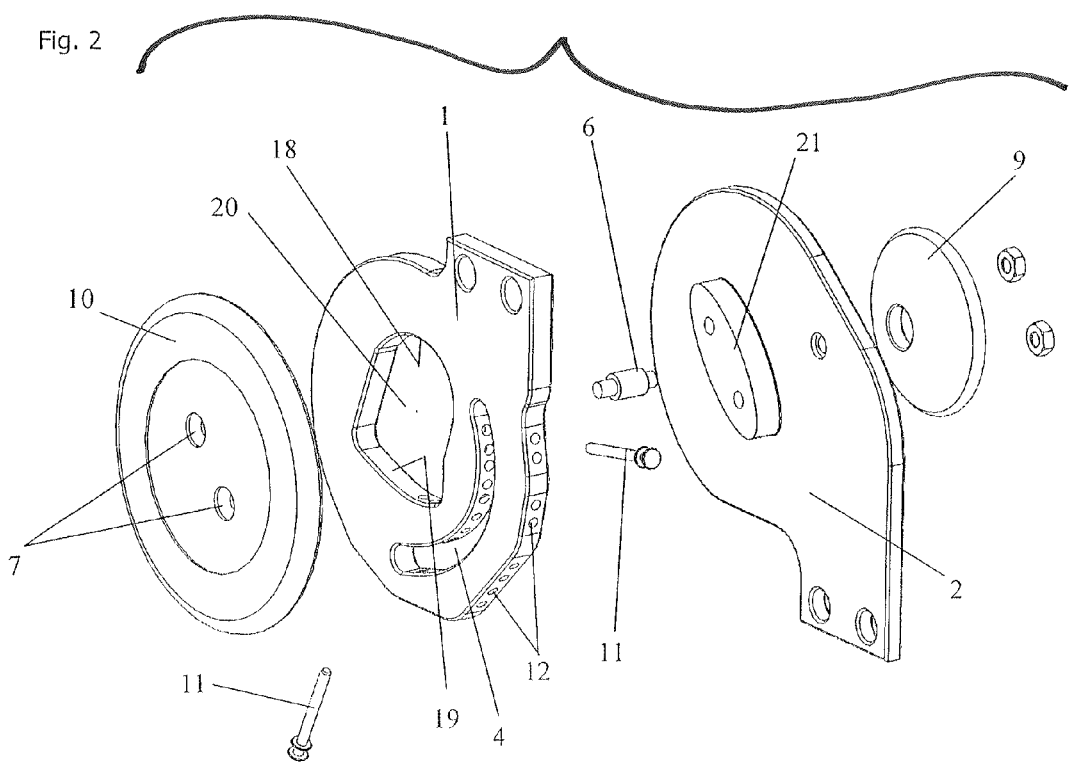
Figure 3:
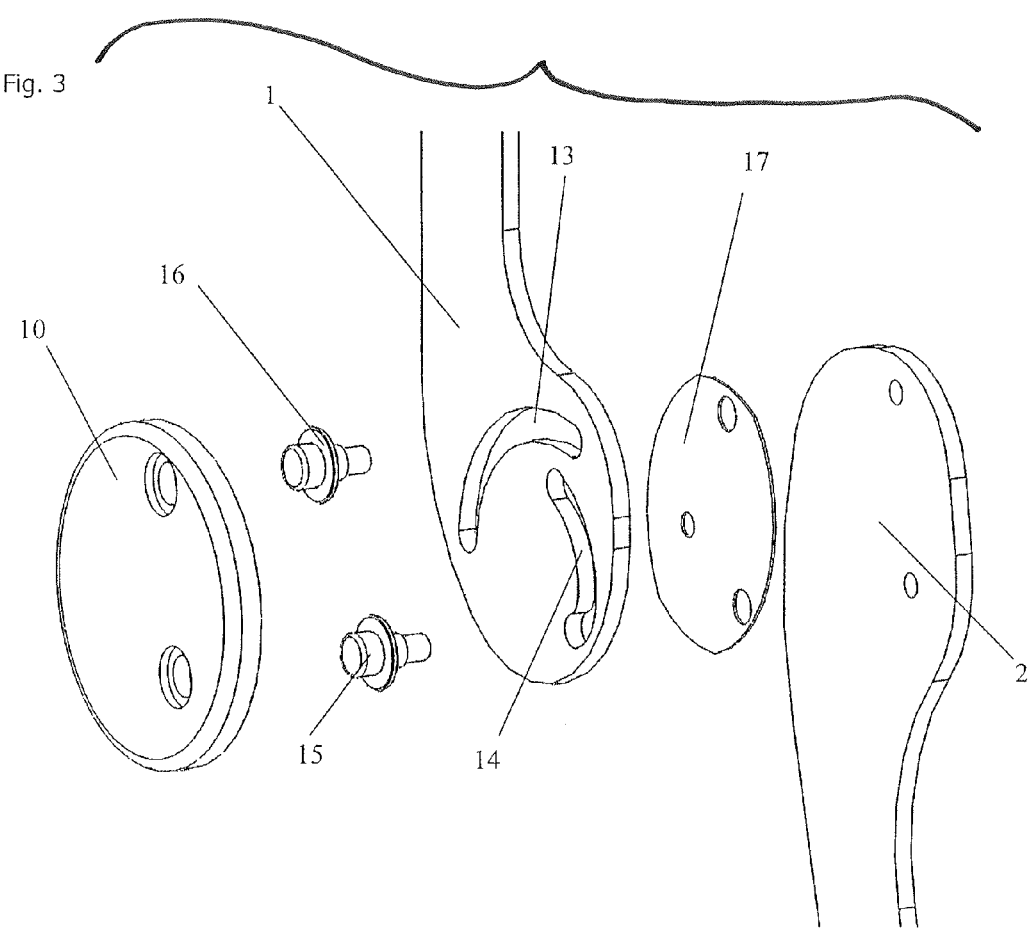
Figure 4:
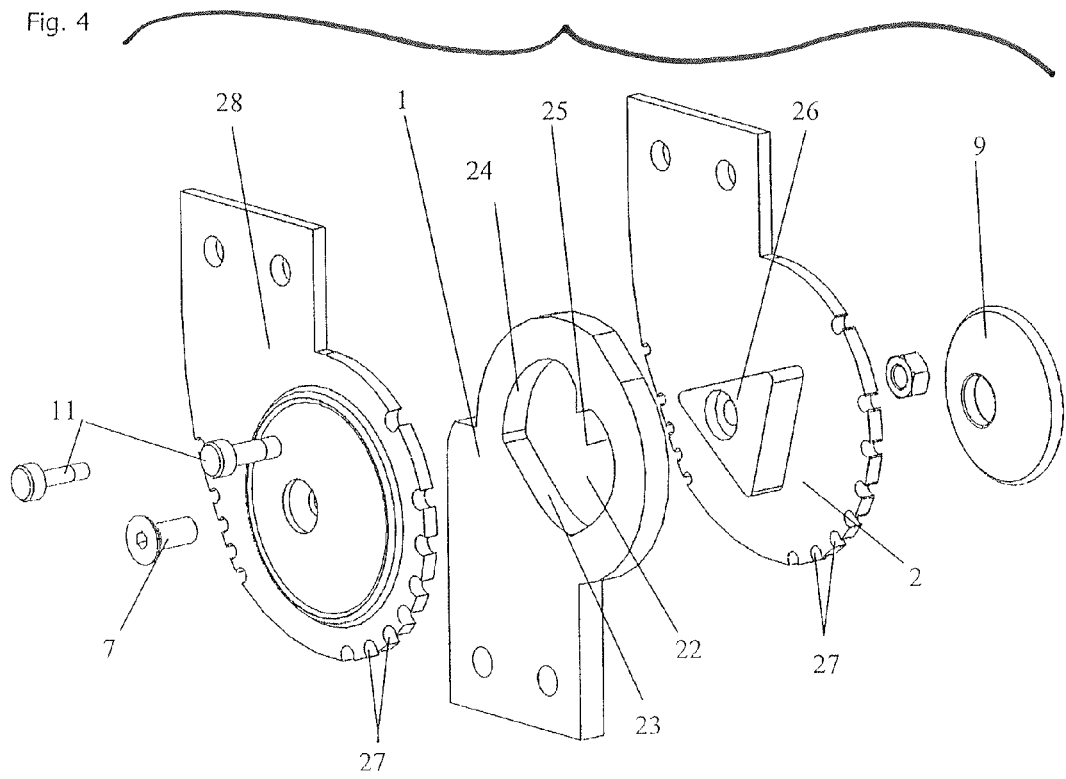

In a knee joint orthosis, in each case two of the hinges according to the invention are used, wherein said hinges can be configured as one piece having longitudinal elements extending along the upper and lower leg of the wearer—see, for example, FIG. 3—or, as in the illustrated exemplary embodiments of the FIGS. 1, 2 and 4, can also be connected by screwing or riveting. The movement of the hinge brackets 1, 2 relative to each other is controlled by the interactive curves 3, 4 in such a manner that the hinge bracket 2 assigned to the upper leg is displaced relative to the hinge bracket 1 assigned to the lower leg from anterior (viewed from the front side of the knee) to posterior, namely such that up to a bending angle of the knee (flexion) of ca. 25 degrees, primarily a rotational movement without visible displacement of the center of rotation takes place towards posterior (rearward), which movement subsequently transitions into a simultaneous rolling and sliding movement with a progressive horizontal displacement of the pivot point between the two hinge brackets 1, 2 to posterior. The resulting bending angle of the hinges according to the invention at the end of the rotation is limited to ca. 120 degrees, but could also reach the maximum bending angle of a knee of up to ca. 135 degrees.

The guide elements 5, 6 can be configured as separate elements, as the guide element 6 in FIG. 1, which are connected to the hinge brackets, for example, by means of screws 7. However, they can also be formed in one piece with the hinge brackets 1, 2, as the guide element 5 in the illustrated example of FIG. 1, through which a screw 8 is extended to connect a first cover disk 9 with a second cover disk 10 and therefore hold the hinge together.

Since often a limitation of the movability between the upper leg and the lower leg of the wearer, in particular of orthoses, is necessary, two pins 11 or similar elements are provided which can be inserted through radial bores 12 in one of the hinge brackets 1, 2 and can be fixed therein. Depending on the placement of the pins 11, the movement of the guide element 6 in the opening 4 and therefore also the range of the possible bending movement of the hinge brackets 1, 2 relative to each other is limited.

The embodiment of the hinge according to the invention according to FIG. 3 also has two openings 13, 14 in the form of slots. Here, both longitudinal openings 13, 14 cut out in the hinge bracket 1 are curved around the pivot point of the generally flat hinge brackets 1, 2 as the center region of the curvature. In each opening 13, 14, one bolt 15, 16 is guided as a guide element, which bolts 15, 16 are connected to the second hinge bracket 2. Through the arrangement and the curvature that changes along the circumference, the physiological rotational movement and progressive sliding movement of the two hinge brackets 1, 2 relative to each other is interactively effected during the rotation, as already described above in connection with FIG. 1.

The two bolts 15, 16 preferably extend through the openings 13, 14 up to the opposite side of the hinge bracket 1 and, in turn, connect the second hinge bracket 2 with a cover plate 10 which holds the hinge brackets 1 and 2 together. A friction-reducing intermediate plate 17 facilitates the relative movement of the two hinge brackets 1, 2.

In order to enable limiting the range of possible bending movement of the hinge brackets 1, 2 relative to each other, an arrangement of bores 27, at least in each case one pin (not illustrated) per hinge bracket 1, 2, and a nose-like projection on each of the hinge brackets 1, 2 are provided. The row of bores 27 in the hinge bracket 1 runs substantially parallel to the slot 13 and runs mirror-imaged thereto in the hinge bracket 2. If now in at least one of the bores 27 a pin is inserted, the projection abuts during the mutual movement of the hinge brackets 1, 2 against this pin and thus blocks further relative movement of the hinge brackets 1, 2. With at least two pins being present, this effect can be achieved for the bending as well as stretching movement. If in each case even two pins are provided per hinge bracket 1, 2, the stability and therefore the safety can be further increased. In the embodiment of FIG. 2, again, the inner wall of the hinge bracket 1 that borders the opening 20 includes two curved guide segments 18, 19. A cam-shaped guide body 21 protrudes into this openinq 20, which guide body is guided with in each case one of its outer sections at in each case one curved guide segment 18, 19. Furthermore, a curved opening 4 is also cut out around the opening 20 as the center. In this opening 4, a guide element 6 secured to the hinge bracket 2 is movably guided and is displaceable therein so as to effect again in this manner and in combination with the effect of the guide body 21 in the opening 20, the movement of the pivot point between the hinge brackets 1, 2, which movement is stationary and subsequently transitions into the combined rolling and sliding movement, as already described above.

The cohesion of the hinge in FIG. 2 is achieved by two screws 7 which are screwed through the cover plate 10 into the guide body 21. The other side of the hinge can be protected again by a cover plate 9. The arrangement of pins 11 and radial bores 12 for limiting the movement of the guide element 6 in the opening 4 and therefore also for limiting the range of the possible bending movement of the hinge brackets 1, 2 relative to each other can also be provided.

In the embodiment of FIG. 4, an opening 22 is cut out in the hinge bracket 1 and is bordered by an inner wall of the hinge bracket 1 having three curved guide segments 23, 24, 25. A triangular guide body 26 which is fixedly connected to the other hinge bracket 2 or is formed thereon engages in this opening 22 in order to effect, by sliding the three outermost regions of the guide body 26 along in each case one of the three curved guide segments 23, 24, 25, the physiological rotating and sliding movement of the two hinge brackets 1, 2 relative to each other.

Likewise, in the embodiment of FIG. 4, as in the case of the embodiment of FIG. 3, limiting the range of the movement of the guide body 26 in the opening 22 and therefore also limiting the range of the possible bending movement of the hinge brackets 1, 2 relative to each other is enabled through an arrangement of pins 11 and bores 27. However, the bores 27 are now displaced all the way to the outer edge of the hinge bracket 2 and to the edge of a cover plate 28, the shape of which substantially corresponds to the hinge bracket 2, so that in the components 2, 28, the bores actually represent grooves which are open radially outward.

A physiologically optimal adaptation of the relative movement of the hinge brackets 1, 2 during the bending or stretching of the leg can also be achieved by an embodiment shown in FIGS. 5a to 5h. Here, a first and essentially straight elongated recess 32 is provided in the first generally flat and p shaped hinge bracket 1. The recess 32 runs essentially parallel to a longitudinal axis of the hinge bracket 1. Within the area of the recess 32, a further essentially straight elongated opening 29 is provided which has a smaller width than the recess 32. The opening, 29 and the recess 32 are essentially perpendicular to each other.

The second generally flat and p-shaped hinge bracket 2 carries two essentially circular guide elements 30, 31 that cooperate with the recess 32 and the opening 29. The first guide element 30 is provided proximately adjacent the hinge bracket 2 and facing the first hinge bracket 1. It is positioned eccentrically and has a diameter corresponding essentially to the width of the recess 32 on the first hinge bracket 1 to be able to turn and to slide along the length of the recess 32. On the first guide element 30 is provided the second guide element 31, which has a diameter corresponding essentially to the width of the straight opening 29 of the first hinge bracket 1. The second guide element 31 is positioned essentially in the center of the generally circular end part of the second hinge bracket 2, which is overlapping with the end part of the first hinge bracket 1. The second guide element 31 can turn and slide along the length of the longitudinal opening 29.

As can be seen from the subsequent positions during the bending movement shown in FIGS. 5d-5h, there is only a slight displacement of the guide element 30 in the recess during the first part of the bending movement of the second hinge bracket 2 assigned to the upper leg in relation to the first hinge bracket 1 assigned to the lower leg. This results in a predominant rotational movement, as can be seen in FIGS. 5d and 5e. Up to a bending angle of the knee (flexion) of ca. 25 degrees, primarily a rotational movement without visible displacement of the center of rotation takes place towards posterior (rearward).

Subsequently, as can be seen in FIG, 5f, continuing the bending movement, a combination of a sliding movement of the guide element 30 in the recess 28 and a sliding movement of the second guide element 31 in slot 29 result in a displacement of the center of rotation of the hinge brackets 1, 2 towards posterior and to a combination of a rotational movement with a linear movement. Starting from a bending angle of the above mentioned appx. 25 degrees, there is a simultaneous rotation and sliding movement with a progressive horizontal displacement of the center of rotation of the hinge brackets 1, 2 towards posterior (backwards). In the last phase of the bending movement, whereby the bending angle of the hinges 1, 2 is again limited to appx. 120 degrees, but could also reach the maximum bending angle of a knee of up to appx. 135 degrees, the movement of the hinge bracket 2 relative to the hinge bracket 1 is essentially only a linear displacement towards posterior (rearward), as can be seen in FIGS. 5g-5h.

The invention claimed is:

1. A hinge for a knee joint orthoses, a knee joint prostheses, or a brace, said hinge comprising:
    a first hinge bracket which is generally flat and includes an opening there through, an inner wall of the first hinge bracket which defines said opening including first and second curved segments, and
    a second hinge bracket which is generally flat and is positioned adjacent to and overlapping with said first hinge bracket, said second hinge bracket mounting a generally triangular guide body which extends into said opening of said first hinge bracket, said generally triangular guide body including three cam-shaped guide corners which contact said first and second curved guide segments of said first hinge bracket to enable combined rotation and sliding movement of said first and second hinge brackets relative to each other in a plane defined therebetween.

2. The hinge according to claim 1, wherein said second hinge bracket is generally p-shaped and includes a generally circular end portion, wherein said generally triangular guide body is connected to said generally circular end portion, and wherein said generally circular end portion includes a plurality of bores along an outer edge thereof.

3. The hinge according to claim 1, including a cover plate positioned adjacent said first hinge bracket opposite said second hinge bracket, and including means to attach said cover plate to said generally triangular guide body of said second hinge bracket.

4. The hinge according to claim 1, wherein said inner wall includes a third curved segment.

5. A hinge for a knee joint orthoses, a knee joint prostheses, or a brace, said hinge comprising:
    a generally p-shaped first hinge bracket which is generally flat and includes a rectilinear recess which extends essentially parallel to a longitudinal axis of said first hinge bracket, and a generally rectilinear opening in a bottom wall of the rectilinear recess, said generally rectilinear opening extending generally perpendicular to said generally rectilinear recess and having a smaller width than a width of the recess, and
    a generally p-shaped second hinge bracket which is generally flat and is positioned adjacent to and overlapping with said first hinge bracket, said second hinge bracket mounting first and second circular guide elements, the first guide element being positioned eccentrically relative to a generally rounded end portion of the second hinge bracket and having a diameter generally corresponding to a width of said recess in the first hinge bracket, and the second guide element being located on the first guide element and having a diameter generally corresponding to the width of the opening in the first hinge bracket, said second guide element extending generally along an axis of the rounded end portion of the second hinge bracket, said first and second hinge brackets being positioned together such that said first guide element extends into said recess and said second guide element extends into said opening to enable combined rotational and sliding movement of said first and second hinge brackets relative to one another relative to a plane defined there between.

\* \* \* \* \*